(12) United States Patent
Hewitson

(10) Patent No.: US 11,471,697 B2
(45) Date of Patent: Oct. 18, 2022

(54) LASER THERAPY DEVICE AND METHOD OF USE

(71) Applicant: Andrew Hewitson, Dana Point, CA (US)

(72) Inventor: Andrew Hewitson, Dana Point, CA (US)

( * ) Notice: Subject to any disclaimer, the term of this patent is extended or adjusted under 35 U.S.C. 154(b) by 0 days.

(21) Appl. No.: 15/838,324

(22) Filed: Dec. 11, 2017

(65) Prior Publication Data

US 2018/0111003 A1  Apr. 26, 2018

Related U.S. Application Data

(63) Continuation-in-part of application No. 14/618,008, filed on Feb. 10, 2015, now Pat. No. 9,839,790.

(51) Int. Cl.
| | |
|---|---|
| *A61N 5/06* | (2006.01) |
| *A61B 18/20* | (2006.01) |
| *A61B 18/00* | (2006.01) |
| *A61N 5/067* | (2006.01) |

(52) U.S. Cl.
CPC .......... *A61N 5/0619* (2013.01); *A61B 18/203* (2013.01); *A61B 2018/00642* (2013.01); *A61B 2018/00791* (2013.01); *A61N 5/067* (2021.08); *A61N 2005/0627* (2013.01); *A61N 2005/0644* (2013.01); *A61N 2005/0651* (2013.01)

(58) Field of Classification Search
None
See application file for complete search history.

(56) References Cited

U.S. PATENT DOCUMENTS

| | | | | |
|---|---|---|---|---|
| 5,336,900 A | * | 8/1994 | Peters | G01S 7/489 250/226 |
| 5,612,779 A | * | 3/1997 | Dunne | G01C 3/08 342/134 |
| 5,726,742 A | * | 3/1998 | Nourrcier | G01S 7/4865 356/5.01 |
| 5,790,241 A | * | 8/1998 | Trussell, Jr. | G01C 3/08 356/4.01 |
| 8,310,655 B2 | * | 11/2012 | Mimeault | G01S 7/487 356/5.01 |
| 8,540,701 B2 | * | 9/2013 | Ferren | A61B 18/203 606/9 |

(Continued)

*Primary Examiner* — Brian T Gedeon
(74) *Attorney, Agent, or Firm* — Kevin Keener; Stephen Presutti

(57) ABSTRACT

A computerized method for controlling the operation of a laser therapy device is disclosed. A laser therapy device comprising laser diodes has a microprocessor for storing and executing instructions pertaining to the operation of the laser diodes within certain parameters. The computerized method detects the movement of the laser therapy device and alters the output of the laser diodes when a movement signal exceeds predetermined threshold parameters. The computerized method detects difference in temperature in certain areas, and patterns in temperature differences, for assistance in diagnosing ailments. The computerized method also detects differences in skin color to determine treatment areas. The computerized method also measures the distance of the laser therapy device to a treatment area. The microprocessor executes instructions then which can alter the output of the laser diodes or generate an alarm signal based on measurements received.

6 Claims, 9 Drawing Sheets

(56) References Cited

U.S. PATENT DOCUMENTS

| | | | |
|---|---|---|---|
| 10,349,997 B1* | 7/2019 | O'Reilly | A61B 90/06 |
| 2004/0122492 A1* | 6/2004 | Harth | A61N 5/0613 |
| | | | 607/88 |
| 2004/0167499 A1* | 8/2004 | Grove | A61B 18/203 |
| | | | 606/9 |
| 2004/0225339 A1* | 11/2004 | Yaroslavsky | A61N 5/062 |
| | | | 607/88 |
| 2005/0096589 A1* | 5/2005 | Shachar | A61B 1/00158 |
| | | | 604/95.01 |
| 2005/0110976 A1* | 5/2005 | LaBelle | G01S 7/4873 |
| | | | 356/5.01 |
| 2005/0154381 A1* | 7/2005 | Altshuler | A61B 18/20 |
| | | | 606/9 |
| 2008/0077200 A1* | 3/2008 | Bendett | A61N 5/0618 |
| | | | 607/89 |
| 2008/0091249 A1* | 4/2008 | Wang | A61N 5/0613 |
| | | | 607/88 |
| 2009/0131922 A1* | 5/2009 | Dewey | A61B 18/203 |
| | | | 606/9 |
| 2009/0171253 A1* | 7/2009 | Davenport | A61N 7/02 |
| | | | 601/2 |
| 2009/0209948 A1* | 8/2009 | Baldacchini | A61N 5/0613 |
| | | | 606/13 |
| 2010/0229748 A1* | 9/2010 | Oron | G01S 17/32 |
| | | | 102/213 |
| 2011/0270365 A1* | 11/2011 | Hamada | A61N 5/0617 |
| | | | 607/90 |
| 2013/0085485 A1* | 4/2013 | Van Valen | A61N 5/0616 |
| | | | 606/9 |
| 2013/0165839 A1* | 6/2013 | O'Neil | A61K 8/0208 |
| | | | 604/1 |
| 2015/0157876 A1* | 6/2015 | Bornstein | A61N 5/0616 |
| | | | 607/90 |
| 2016/0045762 A1* | 2/2016 | Gurovich | A61B 18/203 |
| | | | 607/89 |
| 2019/0015681 A1* | 1/2019 | Pyun | A61B 18/203 |

* cited by examiner

LASER THERAPY DEVICE AND METHOD OF USE

PRIORITY

This application is a continuation in part of, and claims benefit of, U.S. application Ser. No. 14/618,008, filed Feb. 10, 2015, the disclosure of which is hereby fully incorporated by reference.

FIELD OF THE INVENTION

The invention relates generally to laser therapy devices and more particularly to a computerized method for controlling the operation of a laser therapy device.

BACKGROUND OF THE INVENTION

Laser therapy is used in many different treatment scenarios, from Acupuncture through to surgery recovery. The therapeutic value of laser light was discovered by accident. Surgeons noticed that surgeries that were performed using laser scalpels healed faster and better than when using traditional metal scalpels. Furthermore, surgical laser devices required only a simple defocusing of the beam to be used effectively for therapy. Due to this simple re-purposing of existing technology, modern therapy lasers retain much of the engineering design of their surgical cousins.

While each treatment modality uses the same basic laser technology to produce laser light, each has a different requirement for how the light is emitted from the treatment device. Some modalities require tight focus of the beam down to a point (acupuncture), others prefer a larger diffused beam (pain management, wound healing) and certain specialized cases require that the laser light projects the shape of the physiology being treated (for example a long rectangle for treating the spine). Laser beam geometries and the limited capabilities of lenses make it difficult to achieve ideal projections patterns or shapes. Lenses simply take the poor geometry of the laser beam and expand it to a larger version of the poor geometry. Traditionally laser therapy devices use lenses to expand the laser beam, but have limited ability to alter the geometry. Minor differences in the energy level across a laser beam's geometry is magnified as the lens expands the beam. Thus the energy used across the larger area of treatment is not uniform and treatment efficacy is diminished. The operator has to compensate for these deficiencies by "painting" the treatment area. Some devices automatically move the treatment head during use but this approach is costly. Finally, some devices use multiple laser diodes to produce a shotgun effect to cover a larger area of treatment. What is needed is a laser therapy device which can expand the energy of the laser beam into a specific geometric area while at the same time creating a uniform energy distribution across the chosen area.

Laser therapy devices are also becoming increasingly powerful. While this enables greater treatment efficacy, it increases the attendant risks of operating such devices. There are legitimate concerns about using such devices because of the potential to inadvertently injure patients if misused. The high energy level of the beam, if not properly administered, may burn the patient. What is needed is a laser therapy device which automatically regulates the energy output of the laser therapy device during treatment to reduce the risk of such injury.

The present invention is directed toward a cordless, high-powered, laser therapy device. Current high power therapy lasers are based upon surgical lasers, due to the maturity of surgical laser technology. However, surgical lasers were developed to be stationary since they were intended to be used on immobile patients in an operating room environment. There was no requirement to make a surgical laser as a handheld or cordless device.

Although surgical and therapy lasers are almost identical in construction, their uses are very different. These different uses give rise to opportunities for an improved design of a laser device for therapy, but also present engineering hurdles. Specifically;

(1) Surgical lasers are single-modality devices with correspondingly limited operating parameters. Surgical lasers are required to cut tissue to a limited depth. Therapeutic laser devices on the other hand are used for many different inidications.

(2) When used for therapy, laser treatment exhibits so-called "dose dependence". This means that higher treatment doses generally produce an improved therapeutic outcome. Thus there is a tendency to use higher power laser therapy devices as this improves both treatment outcomes and the time (and cost) efficiency of treatment.

(3) Surgical lasers require a single narrow beam of light. Therapy lasers require a dispersed beam. Additionally, therapy lasers with a dispersed beam improve safety.

(4) Surgical lasers require exact control of power output as this determines the depth of cut. Therapy lasers are concerned more with "dose" or accumulated radiation, so lower power can be used at the expense of longer treatment time.

(5) Surgical lasers are required to heat tissue so hot that it evaporates, whereas therapy lasers must not be allowed to cause discomfort or tissue damage.

(6) Surgical lasers are directed at a very small area, whereas therapy lasers are frequently used to "paint" a treatment area. This results in higher probability of stray radiation.

Laser therapy devices vary principally in output power. The range is a few milli-Watts to tens of Watts. Like any light source, a laser diode is not 100% efficient. Waste energy is liberated as heat, so thermal management for high-power laser therapy devices is a significant engineering hurdle. Modern laser diodes are around 50% efficient. Thus 50% of the electrical power is converted to light output and the other 50% is converted to heat. In high power laser therapy devices, this "waste" heat presents two engineering concerns. The first is that a laser diode's efficiency and life degrade at elevated temperatures. The second is that dumping heat into the surrounding air requires a bulky cooling apparatus. Device overheating and optical fiber coupling problems are the major causes of device failure.

High power laser therapy devices consume significant electrical power. In order for a laser therapy device to operate as a cordless device, large batteries are required. This causes such a device to be overly bulky and perceived as impractical. Because of these hurdles, laser therapy devices have historically been tethered to a base station.

Therapy lasers have historically been repurposed surgical lasers. Manufacturers have simply applied different optical heads and software to these devices to diverge the beam. Although some of these devices are portable, they are only portable in that all the components can be moved from one location to another with relative ease. There has been no self-contained, high power, handheld laser therapy unit. No manufacturer has yet designed and implemented a therapy laser from scratch because of the comparative ease of repurposing surgical lasers. For this reason, the invention and advances described herein are nonobvious. Otherwise the advances described herein would already be available on the market.

The present invention overcomes these limitations. One embodiment of the invention is directed toward a cordless, high-powered, laser therapy device. "High-powered" means any optical power output by the laser therapy device that emits light output of five (5) Watts or higher, although the same technology can be employed to benefit lower power devices. The cordless, handheld, embodiment of the laser provides a great advantage in situations where a patient requires treatment in a specific position which would be awkward or impractical to treat with a corded device. Likewise, a cordless, handheld, laser therapy unit would be beneficial for treating animals in the care of a veterinarian.

Due to the limitations in the current state of the art, handheld laser therapy devices are unable to be high powered. Laser diodes typically require around 20% of the maximum electrical power before they start emitting light. Therefore at low output power levels the conversion rate of electrical power to optical power is very low. The power requirement therefore becomes overtly high just to be able to emit a small amount of light.

The current invention uses a novel approach for improving efficiency of the laser diodes at lower output power requirements (and therefore minimizing electrical consumption). The maximum efficiency of the laser diodes is when they are operating at maximum specified output power. The invention employs two mechanisms for adjusting the total output power of the device while the laser diodes are running at maximum output. Firstly, the invention disables a portion of the array of diodes. Those laser diodes that are switched on are operating at 100% of output but since there are fewer, the net light output is reduced. The second mechanism is to pulse the diodes between off and on at high frequency and to vary the percentage of time that the diode is in the "on" state. This technique of "Pulse Width Modulation" is used to provide a much finer degree of control than selective disabling of parts of the laser diode array. These two power control methods are using in addition to the typical proportional control of the laser diode's output.

The current invention also allows the laser to be controlled by a computer to allow for easier use by an operator. The invention controls the operation of the laser diode array only within specific parameters. This allows an operator to utilize the laser therapy device without risk of injury to a patient and thus improves the operation of the laser therapy device.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The invention is directed toward a computerized method for managing the operations of a laser therapy device. In one embodiment the computerized method comprises emitting one or more laser beam pulses from one or more rangefinder units; receiving, by one or more rangefinder units, one or more returning target reflections of one more laser beam pulses; determining a time of flight for each of one or more returning target reflections; determining, by one or more microprocessors, a distance from one or more laser rangefinder units to a reflecting treatment area; transmitting a distance reading from one or more laser rangefinder units to one or more microprocessor units; and comparing, by one or more microprocessor units, said distance reading to a predetermined distance.

The computerized method may further comprise altering, by one or more microprocessor units, a laser output of one or more laser diodes when a distance reading exceeds one or more predefined distance parameters. The computerized method may further comprise generating, by one or more microprocessor units, an alarm signal when said distance reading exceeds one or more predefined distance parameters. The computerized method may further comprising receiving, by one or more microprocessor units, an instruction to adjust one or more predetermined distance parameters.

In another embodiment of the invention, the computerized method comprises transmitting one or more movement signals from one or more inertial measurement units to one or more microprocessor units. The computerized method may further comprise altering, by one or more microprocessor units, a laser output of one or more laser diodes when one or more movement signals exceeds one or more predetermined movement parameters. The computerized method may further comprise generating, by one or more microprocessor units, an alarm signal when one or more movement signals exceeds one or more predetermined movement parameters. The computerized method may further comprise receiving, by one or more microprocessor units, an instruction to adjust one or more predetermined movement parameters.

In another embodiment the computerized method comprises measuring, by a temperature sensor, a first temperature reading comprising a temperature of an area to be subjected to an output of one or more laser diodes; measuring, by said temperature sensor, a second temperature reading comprising a temperature of an area adjacent to said area to be subjected to an output of one or more laser diodes; transmitting said first temperature reading from said temperature sensor to one or more microprocessor units; transmitting said second temperature reading from said temperature sensor to one or more microprocessor units; and comparing, by one or more microprocessor units, said first temperature reading to said second temperature reading. The computerized method may further comprise altering, by one or more microprocessor units, a laser output of one or more laser diodes when a difference between said first temperature reading and said second temperature reading exceeds a threshold amount. The computerized method may further comprise generating, by one or more microprocessor units, an alarm signal when a difference between said first temperature reading and said second temperature reading exceeds a threshold amount. The computerized method may further comprise receiving, by one or more microprocessor units, an instruction to adjust a threshold amount of difference between said first temperature reading and said second temperature reading.

In another embodiment of the invention the computerized comprises measuring, by one or more color measurement devices, a first visual color reading comprising a color of an area to be subjected to an output of one or more laser diodes; transmitting said first visual color reading from one or more color measurement devices to one or more microprocessor units; and comparing, by one or more microprocessor units, said first visual color reading to a baseline visual color reading.

The computerized method may further comprise measuring, by one or more color measurement devices, one or more second visual color readings comprising a color of areas adjacent to said area to be subjected to an output of one or more laser diodes; transmitting one or more second visual color readings from one or more color measurement devices to one or more microprocessor units; and generating, by one or more microprocessor units, said baseline visual color reading. The computerized method may further comprise altering, by one or more microprocessor units, a laser output of one or more laser diodes when a difference between said first visual color reading and said baseline visual color reading exceeds a threshold amount. The computerized method may further comprise generating, by one or more microprocessor units, an alarm signal when a difference between said first visual color reading and said baseline visual color reading exceeds a threshold amount The computerized method may further comprise receiving, by one or more microprocessor units, an instruction to adjust a threshold amount of difference between said first visual color reading and said second baseline visual color reading.

In another embodiment of the invention the computerized method comprises receiving, by one or more microprocessor units, a grip sensor signal; and preventing, by one or more microprocessor units, the emission of radiation from one or more laser diodes when one or more microprocessor units fails to receive a grip sensor signal. The computerized method may further comprise determining an amount of time since a last received grip sensor signal. The computerized method may further comprise altering, by one or more microprocessor units, a laser output of one or more laser diodes when said amount of time exceeds a predetermined amount of time. The computerized method may further comprise receiving, by one or more microprocessor units, an instruction to adjust said predetermined amount of time.

In another embodiment of the invention the computerized method comprises simultaneously measuring, by a plurality of temperature sensors, a plurality of independent temperature readings; generating, by said one or more microprocessor units, a pattern of said plurality of independent temperature readings; and comparing, by said one or more microprocessor units, said pattern of said plurality of independent temperature readings to a predetermined pattern of temperature readings. The computerized method may further comprise altering, by said one or more microprocessor units, a laser output of one or more laser diodes based upon comparison results. The computerized method may further comprise generating, by said one or more microprocessor units, an alarm signal based upon comparison results. The computerized method may further comprise receiving, by said one or more microprocessor units, an instruction to adjust comparison results.

Still other embodiments of the present invention will become readily apparent to those skilled in this art from the following description wherein there is shown and described the embodiments of this invention, simply by way of illustration of the best modes suited to carry out the invention. As it will be realized, the invention is capable of other different embodiments and its several details are capable of modifications in various obvious aspects all without departing from the scope of the invention. Accordingly, the drawing and descriptions will be regarded as illustrative in nature and not as restrictive.

BRIEF DESCRIPTION OF THE DRAWINGS

Various exemplary embodiments of this invention will be described in detail, wherein like reference numerals refer to identical or similar components, with reference to the following figures, wherein.

DETAILED DESCRIPTION OF THE PREFERRED EMBODIMENT

The claimed subject matter is now described with reference to the drawings. In the following description, for purposes of explanation, numerous specific details are set forth in order to provide a thorough understanding of the claimed subject matter. It may be evident, however, that the claimed subject matter may be practiced with or without any combination of these specific details, without departing from the spirit and scope of this invention and the claims.

As used in this application, the terms "component", "module", "system", "interface", or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component.

Figure 1:
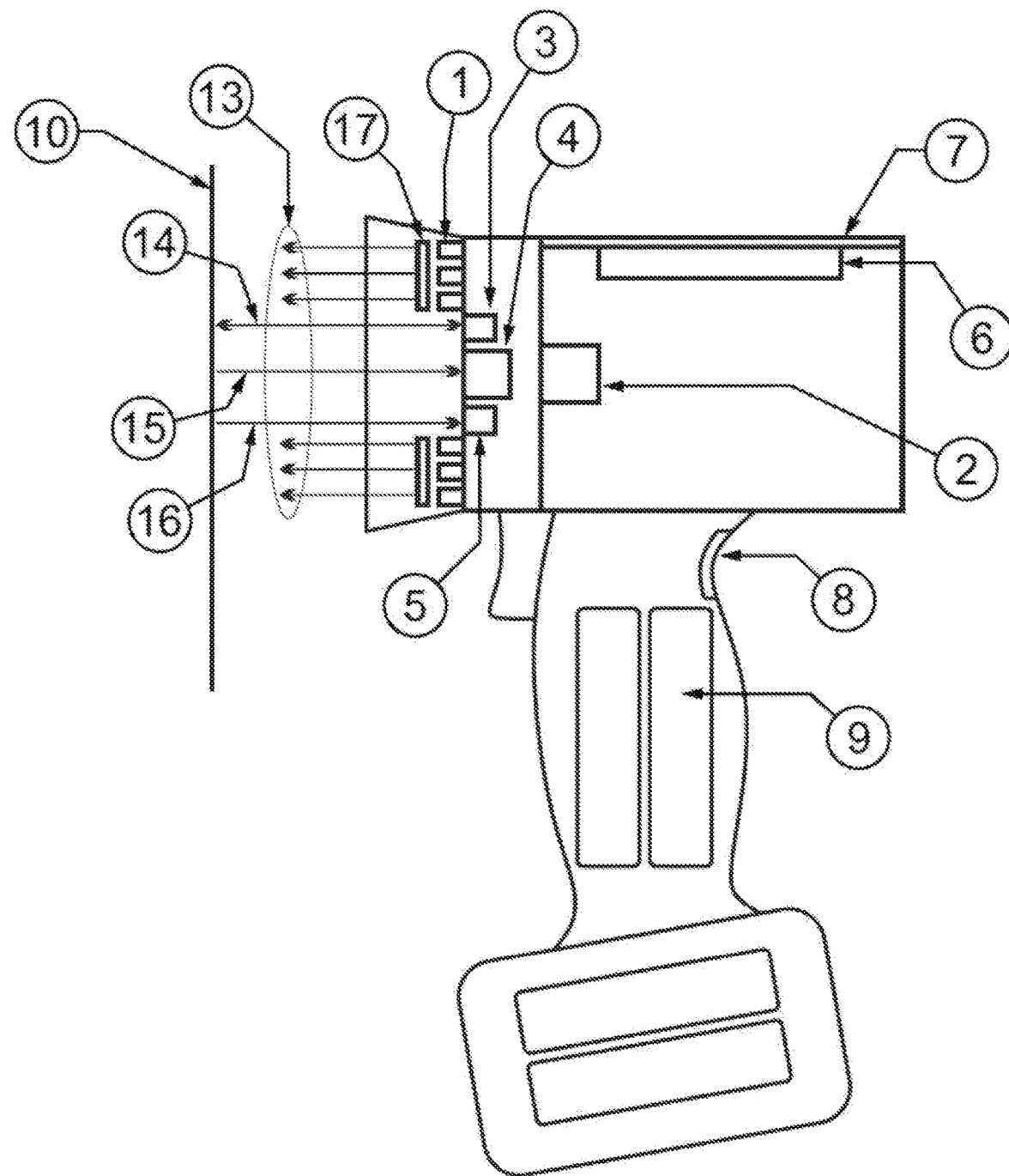
FIG. 1 is a schematic of the preferred embodiment of the laser therapy device.

The invention is directed toward a computerized method for controlling the operations of a laser diode array for a laser therapy device. Referring to FIG. 1, the preferred embodiment of the laser therapy device is illustrated. In this embodiment the laser therapy device comprises a light source 1, an inertial measurement unit 2, a range finder 3, temperature sensor 4, a color measurement device 5, a microprocessor unit 6, a user interface 7, a grip sensor 8, a power source 9, and an optics components 17. The laser therapy device emits radiation 13 from the light source 1. The radiation 13 is applied to the treatment area 10 of the patient. The treatment area 10 may be any location on the external surface of the skin of the patient or may be a subdermal location.

The laser therapy device may be found in any configuration. The light source 1 may be any type of light emitting diode. In the preferred embodiment the light source 1 is a laser diode. The laser therapy device may utilize any number of light sources 1.

The inertial measurement unit 2 is a component which measures the movement and position of the laser therapy device. The inertial measurement unit 2 may be an accelerometer which measures the movement of the laser therapy device, a gyroscope which measures the position and angle of the laser therapy device, or both.

The range finder 3, is a component which measures the distance from the range finder 3 to the treatment area 10. The range finder 3 can measure the distance between the range finder 3 and the treatment area by any means, such as triangulation or time of flight of a signal. In the preferred embodiment the range finder 3 determines the distance by emitting a distance signal 14 which is reflected off of the treatment area 10 and received by the range finder 3. The range finder 3 determines the distance by determining the time of flight of the distance signal 14. The distance signal 14 may be a laser light or sound pressure waves. In the preferred embodiment the range finder 3 utilizes a laser light beam to determine the distance to the treatment area 10, similar to the method disclosed in U.S. Pat. No. 5,790,241 (Trussel, Jr.), the disclosure of which is hereby fully incorporated by reference. The laser range finder 3 is an improvement over utilizing solely a thermal imaging camera to determine if the laser therapy device is pointed at tissue since hair and clothing can prevent thermal radiation from being detected.

The temperature sensor 4 is any type of component which measures the temperature of the treatment area 10. In the preferred embodiment the temperature sensor is a non-contact fair infrared temperature sensor array. There may be one or more temperature sensors 4. In the preferred embodiment the temperature sensor 4 detects and measures infrared emissions 15 from the treatment area.

The color measurement device 5 is any component which measures the color of the treatment area 10. In the preferred embodiment the color measurement device 5 is a camera which detects and measures visible light 16 reflected off of the treatment area 10. The color measurement device 5 may also be a receptor chip which measures the amount and value of green light, blue light, and red light received to determine a color value. The color measurement device 5 may also be a component which measures the wavelength of light received.

The microprocessor unit 6 is any type of computer processing unit. In the preferred embodiment the microprocessor unit 6 is a master control unit which stores instructions for operations of the laser therapy device. In other embodiments the microprocessor unit 6 stores information on a database separate from the microprocessor unit 6.

The user interface 7 is any type of component which allows the user to obtain information about the laser therapy device or provide instructions to the laser therapy device. In the preferred embodiment the user interface 7 is a touch screen interface. In other embodiments the user interface 7 may be a plurality of knobs. In other embodiments the laser therapy device may have a display screen which is separate from the user interface 7.

The grip sensor 8 is a component which determines that a user is holding the laser therapy device. The grip sensor 8 may be located at any position on the laser therapy device. In the preferred embodiment the grip sensor 8 is positioned on the handle of the laser therapy device in a location where a hand is certain to encounter the grip sensor 8. The grip sensor 8 may operate in any manner to determine that a user is holding the laser therapy device. The grip sensor 8 may be an electrical contact that changes resistance when it comes in contact with human skin. The grip sensor 8 may be a switch that is depressed when a user holds the laser therapy device. The grip sensor 8 may also be a piezoelectric contact which generates an electrical signal when distorted by a user's hand. Other embodiments of the grip sensor 8 may be utilized provided that the grip sensor 8 delivers a signal to the microprocessor unit 6 (or ceases delivering a signal) when a user is holding the laser therapy device.

The power source 9 is any type of component which provides power for the operation of the laser therapy device. In the preferred embodiment the power source 9 is a rechargeable battery pack. The power source 9 may also be replaceable batteries.

The optics components 17 are one or more specific optical elements which may be arranged in any pattern to form the radiation 13 from the light source 1 into a specific geometric pattern. In the preferred embodiment, the beam forming optics components 17 are a combination of diffractive optical elements (such as lenses and prisms which have the ability to shape the beam of light into a specific shape), refractive optical elements, and diffusive optical elements. The diffractive optical elements and diffusers are more versatile and efficiently convert an incident beam into a specific geometric shape with specific energy distribution across a specific pattern. When the light source 1 is an array of laser diodes, the microprocessor 6 may be programmed to adjust the output of each individual laser diode so that a specific pattern of radiation 13 is formed with specific energies formed at specific locations within the pattern of radiation 13. The optics components 17 may contain a specific identification and send an identification signal to the microprocessor 6. Based on the received identification signal, the microprocessor 6 then respectively adjusts the output of the specific laser diodes in the array.

Figure 2:
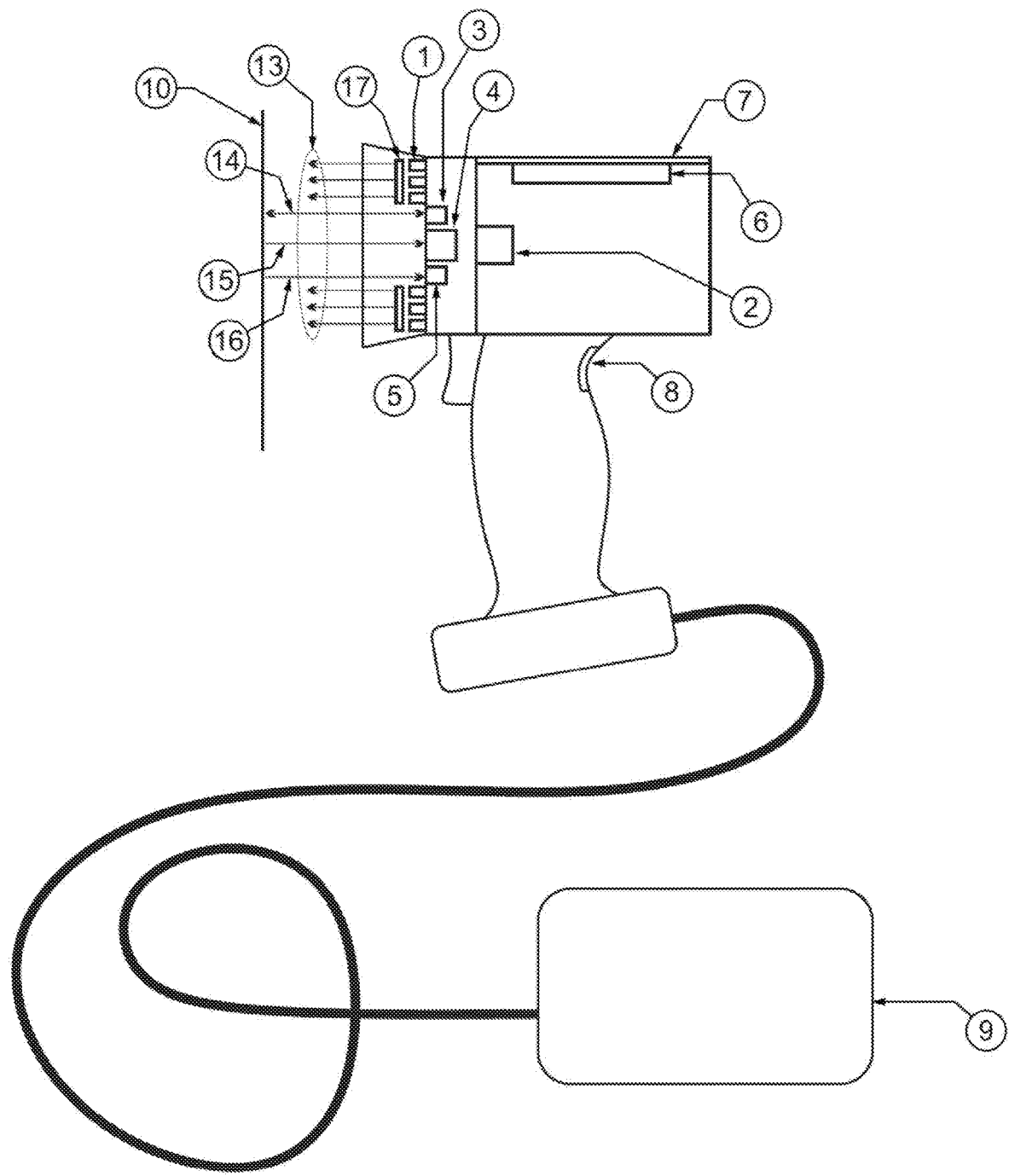
FIG. 2 is a schematic of an alternative embodiment of the laser therapy device.

Referring to FIG. 2, an alternative embodiment of the laser therapy device is illustrated. In this embodiment the power source 9 is external from the body of the laser therapy device and is connected by a cable to provide power to the laser therapy device. In this embodiment the power source 9 may be a battery or an outlet which the laser therapy device is plugged into.

Figure 3:
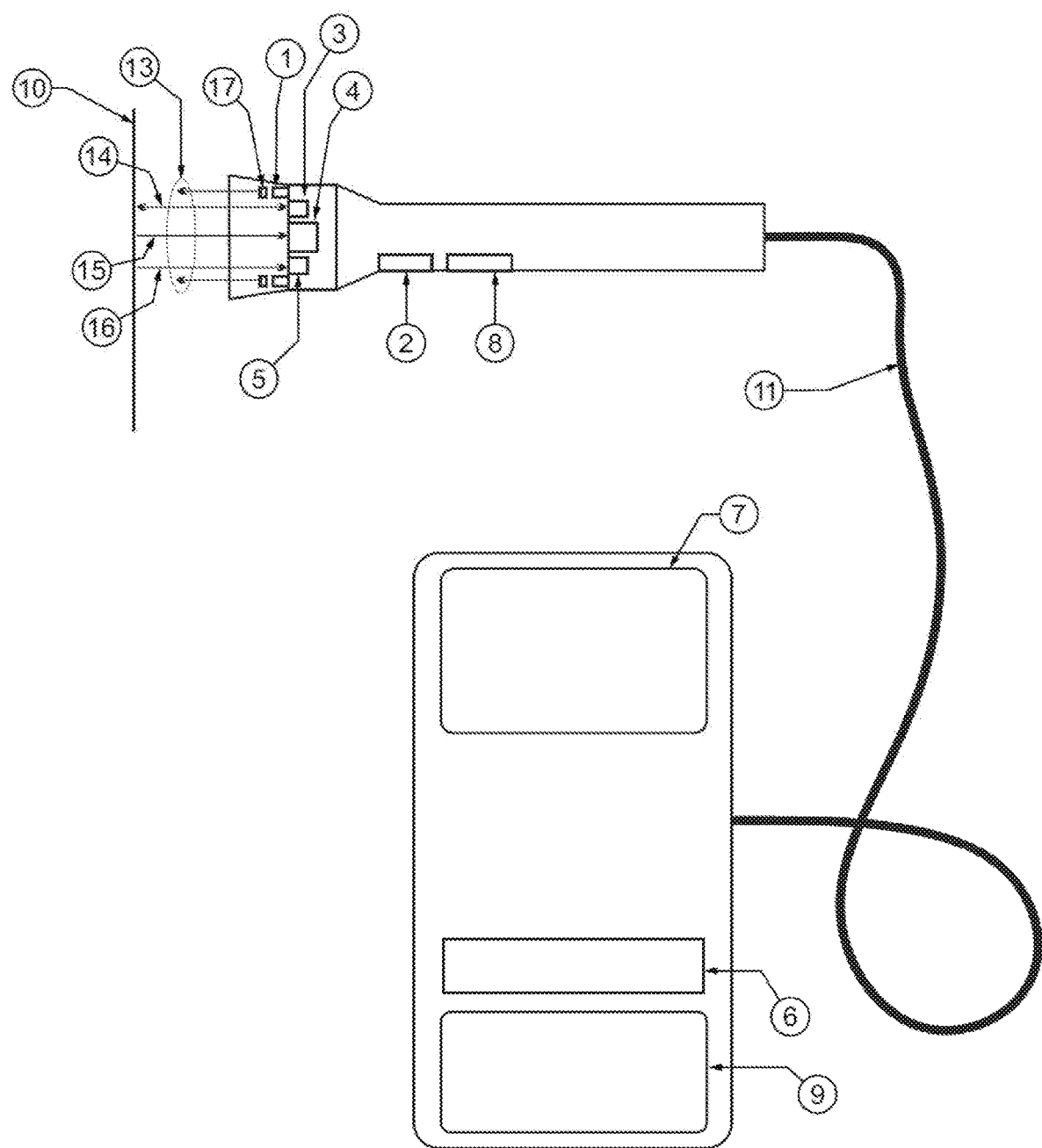
FIG. 3 is a schematic of an alternative embodiment of the laser therapy device.

Referring to FIG. 3, an alternative embodiment of the laser therapy device is illustrated. In this embodiment the laser therapy device is configured as a wand which is connected to a base unit by a cable 11. In this embodiment the base unit houses the microprocessor unit 6, the user interface 7, and the power source 9. The power source 9 may be a battery or an outlet which the base unit is plugged into. The base unit provides power to the wand of the laser therapy device by a cable 11.

Figure 4:
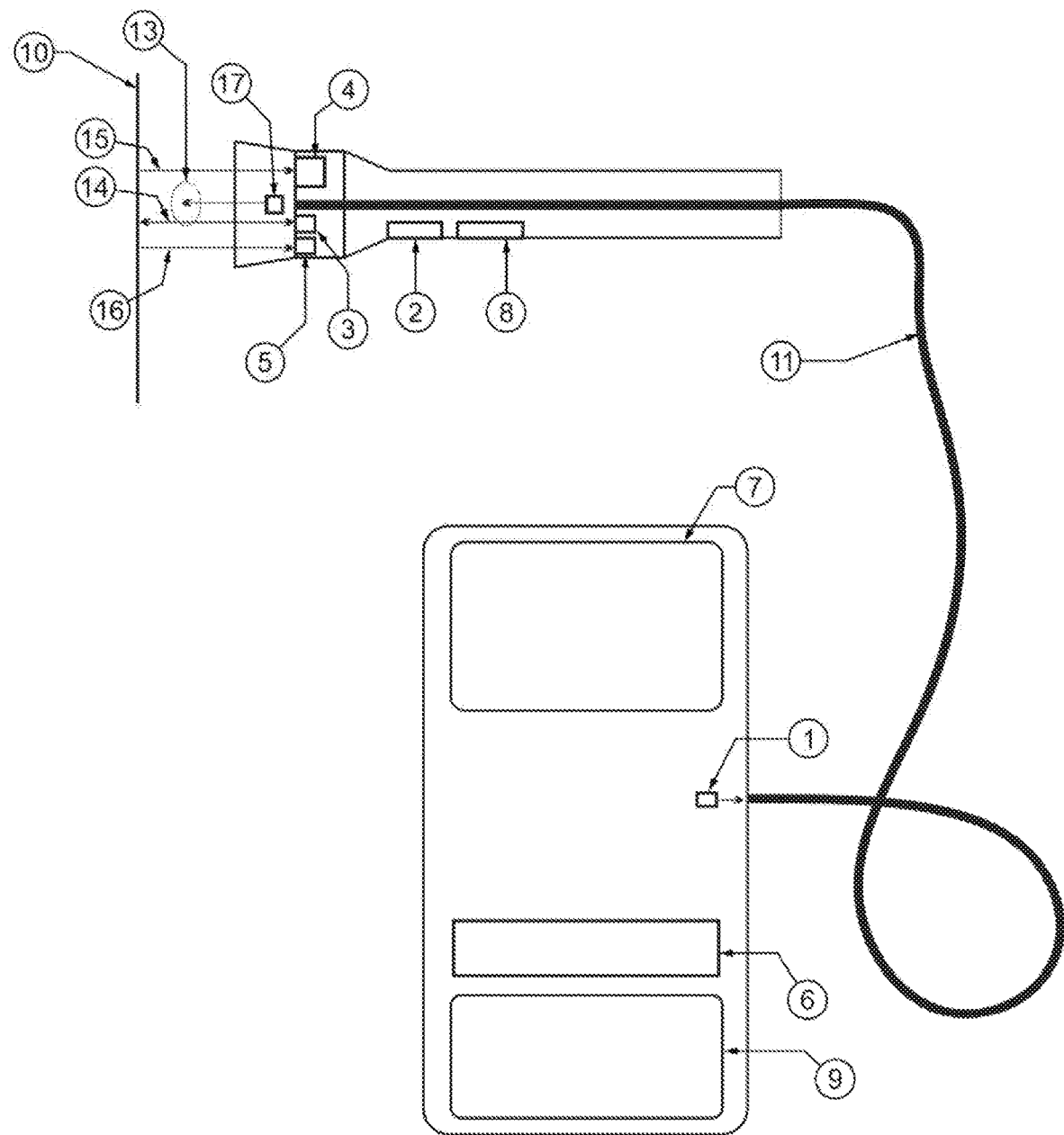
FIG. 4 is a schematic of an alternative embodiment of the laser therapy device.

Referring to FIG. 4, and alternative embodiment of the laser therapy device is illustrated. In this embodiment the base unit also houses the light source 1. In this embodiment the radiation 13 from the light source travels through a fiber optic cable in the cable 11.

The computerized method of the invention may be utilized in any configuration of the laser therapy device illustrated. One skilled in the art would appreciate that the method could also be utilized in other configurations of a laser therapy device.

Figure 5:
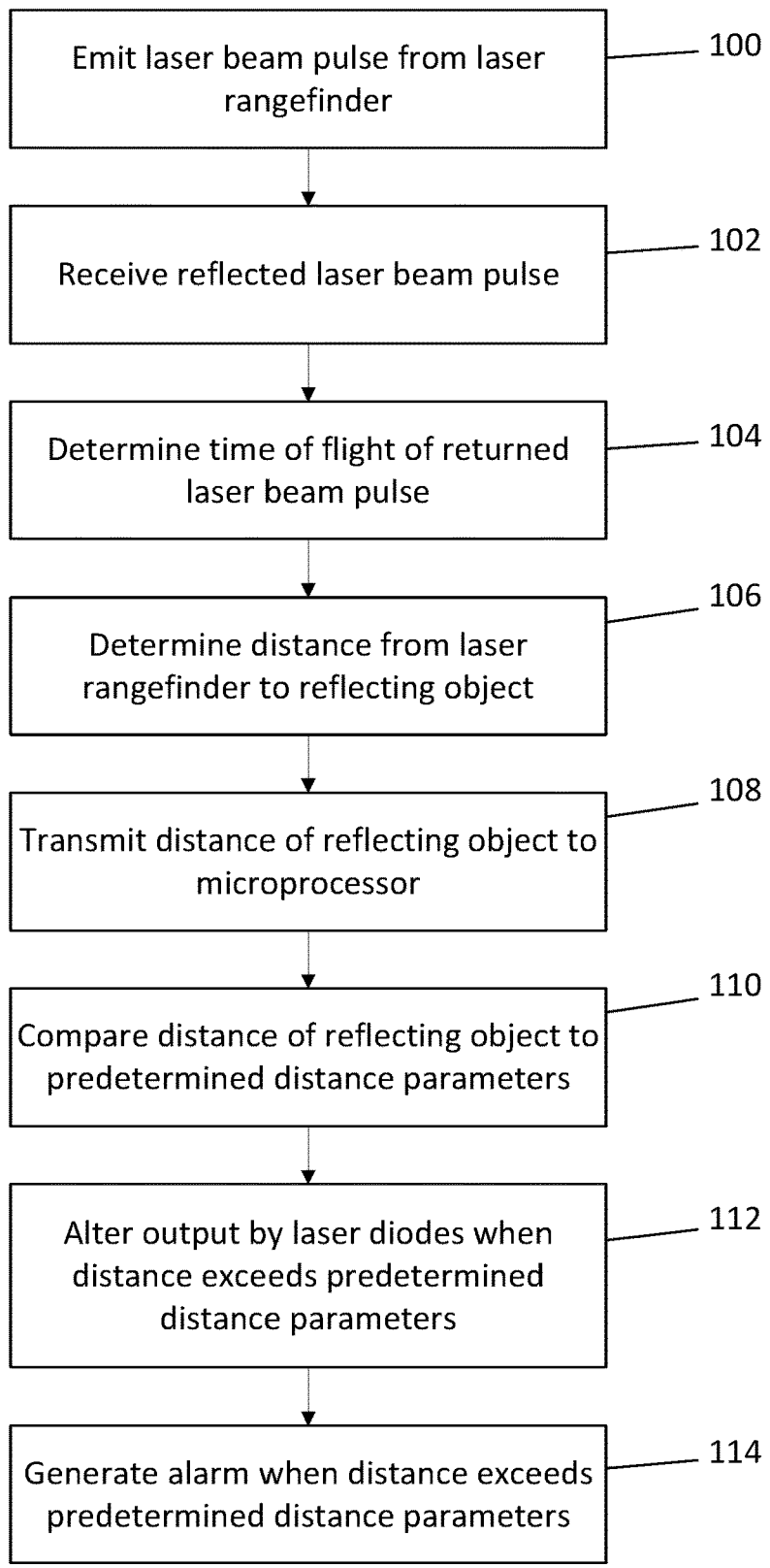
FIG. 5 is schematic of the method of the operation of the laser therapy device.

Referring to FIG. 5, the computerized method for utilization of the range finder 3 is illustrated. First the range finder emits a laser beam pulse 100. The range finder receives a reflected laser beam pulse 102. The range finder determines the time of flight of the returned laser beam pulse 104. The range finder determines the distance of the treatment area to the range finder 106. The range finder transmits the distance of the reflecting object to the microprocessor 108. The microprocessor compares the distance to a set of predetermined distance parameters 110. For instance, the microprocessor may store a minimum distance and a maximum distance of the laser therapy device to the treatment area. The microprocessor then alters the output of the laser diode when the distance exceeds the predetermined distance parameters 112. In addition, the microprocessor may cause the laser therapy device to generate an alarm when the distance exceeds the predetermined distance parameters 114. The microprocessor may diminish the output of the laser diode by a certain percentage or may completely disable the laser diode. The microprocessor may have multiple sets of predetermined distance ranges—with each predetermined distance causing a separate alteration of the laser diode. For instance, the predetermined distance range for optimal operation may be three to five inches. Within this range the output of the laser diode is 100%. There may be and additional predetermined range distance of two to three inches and five to six inches where the output of the laser diodes is set to 50%. When the distance is determined to be shorter than two inches or longer than six inches the microprocessor completely stops the operation of the laser diodes. If an alarm is generated, the laser therapy device may generate any type of alarm, such as vibrating, sounding an audible alarm, or flashing one or more lights. The alarm may vary depending on the amount of difference between the measured distance and the predetermined distance parameters. The predetermined distance parameters may be any distance and may be varied based on instructions provided to the microprocessor. The distance parameters are any information which affects the optimal distance of the laser therapy device to the treatment area. The distance parameters may include species of animal being treated, specific condition being treated, and area of the body being treated. The optimal distance is determined algorithmically based upon the distance parameters and other parameters of operation.

Figure 6:
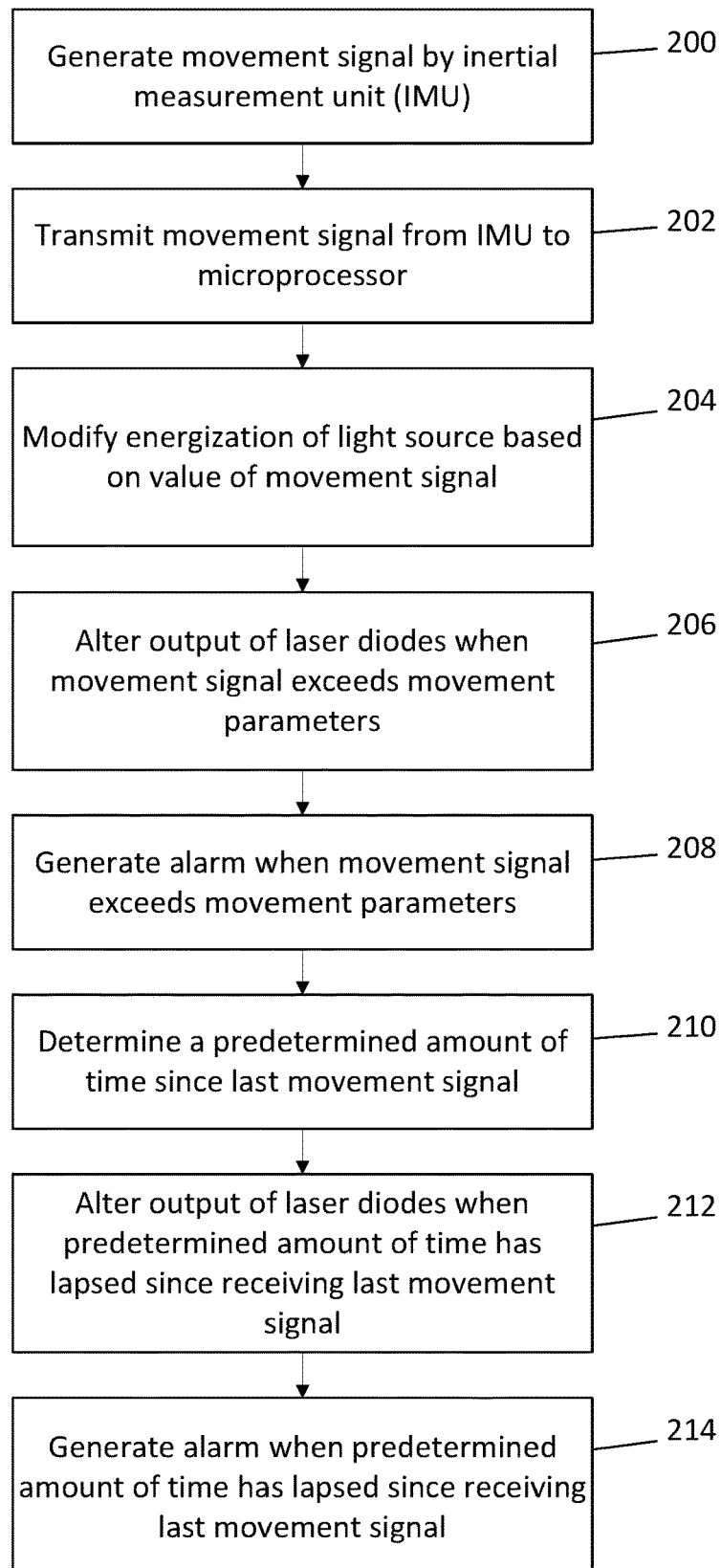
FIG. 6 is schematic of the method of the operation of the laser therapy device.

Referring to FIG. 6, the computerized method of utilization of the inertial measurement unit 2. The inertial measurement unit (IMU) generates a signal when it detects movement of the laser therapy device 200. The movement signal may be directly proportional to the amount of displacement, speed of movement, frequency of movement, or sudden stops. The IMU transmits the movement signal to the microprocessor 202. The microprocessor prevents the operation of the laser diode unless the movement signal exceeds a predetermined threshold of motion 204. In this manner the microprocessor may prevent the accidental emission of radiation if a user has not picked up and moved the laser therapy device into position. During use the microprocessor alters the output of the laser diode if it determines that the movement signal exceeds a set of predetermined parameters 206. For instance, if the operator accidentally drops the laser therapy device then the IMU sends a signal to the microprocessor. The microprocessor determines that the movement exceeds the acceptable level of movement and stops the operation of the laser diode. There may be multiple sets of movement parameters where the operation of the laser diodes is altered by a predetermined percentage. The microprocessor may also cause the laser therapy device to generate an alarm when the movement signal exceeds the predetermined movement parameters 208. The movement parameters may be any information related to the movement or lack of movement of the laser therapy device. The movement parameters may include sudden movement, lack of movement, position of the laser therapy device, amount of time that the laser therapy device is in a specific position, displacement, acceleration, frequency of movement, amount and severity of vibrations, or any other information related to the movement of the laser therapy device. The movement signal would be determined to "exceed" the predetermined movement parameters if the movement is opposite of the established parameters. For instance, if the movement parameters require a lack of movement for the proper operation of the laser therapy device then the movement signal exceeds the predetermined movement parameters when the movement signal determines that there has been movement. The opposition would also be true, if the predetermined movement parameters require movement (such as to prevent injury if the laser therapy device is not moved) then the movement signal exceeds the parameters when it determines that there is a lack of movement.

The inertial measurement unit 2 may also include a gyroscope to determine the position of the laser therapy device. The gyroscope sends a position signal to the microprocessor. The microprocessor may also generate an alarm or alter the output of the laser diodes when the position of the laser therapy device exceeds a predetermined range of positions. In this manner if the laser therapy device is held upside down then the microprocessor prevents the laser diode from emitting radiation.

The microprocessor may also prevent damage to tissue by altering the output of the laser diodes if an operator does not move the laser therapy device after a predetermined amount of time. In this manner the microprocessor determines a predetermined amount of time has passed since it has received a movement signal 210. The microprocessor alters the output of the laser diodes when a predetermined amount of time has passed 212. There may be more than one predetermined amounts of time such that the output is decreased in increments over time. In addition, the microprocessor may cause the laser therapy device to generate an alarm when the predetermined amount of time has passed 214.

Figure 7:
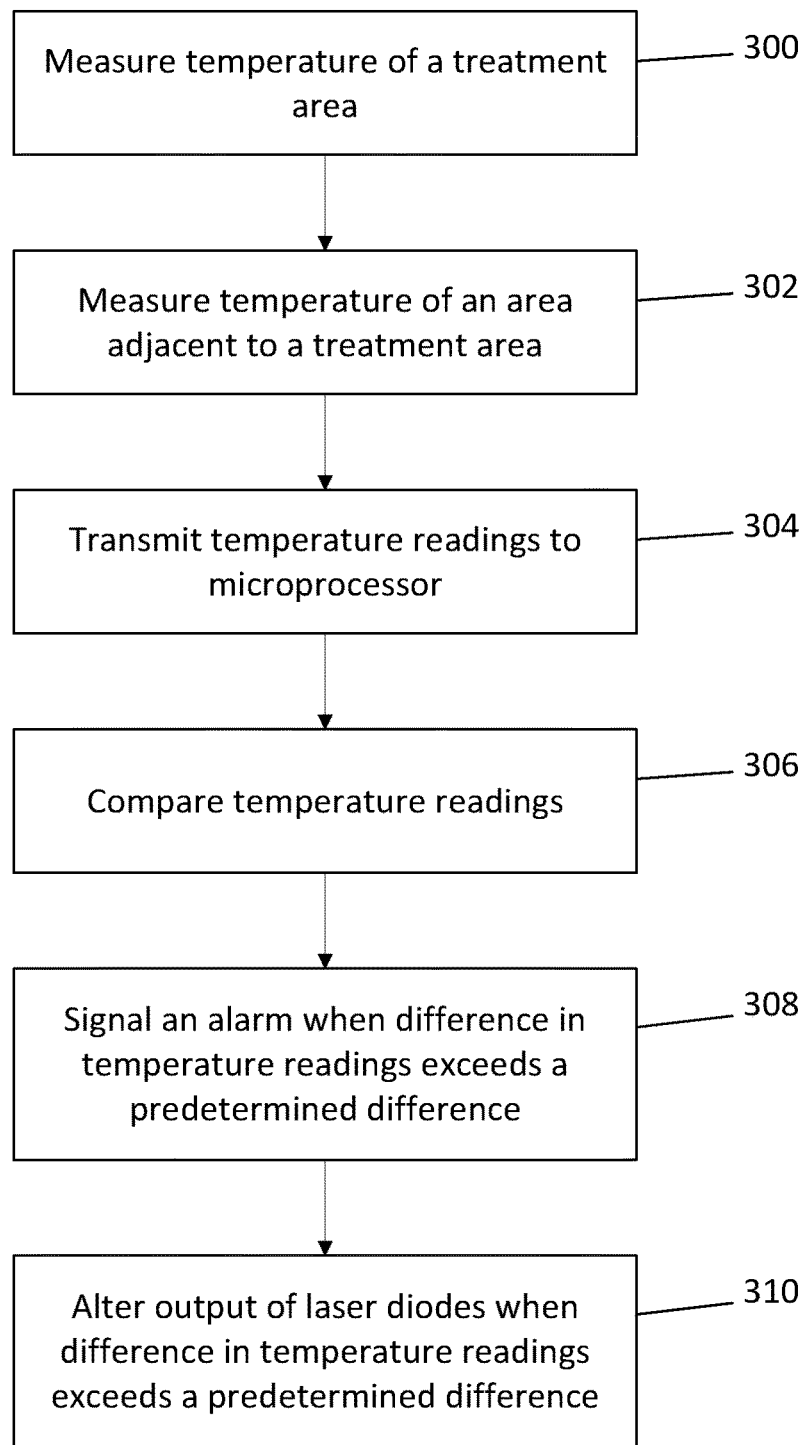
FIG. 7 is schematic of the method of the operation of the laser therapy device.

Referring to FIG. 7, the computerized method of the operation of the temperature sensor 4 is illustrated. The temperature sensor measures the temperature of a treatment area 300. The temperature sensor also measures the temperature of an area adjacent to the treatment area 302. The temperature sensor transmits the temperature readings to the microprocessor 304. The microprocessor then compares the two temperature readings 306. The microprocessor may cause the laser therapy device to signal an alarm when the difference in the temperature readings exceeds a predetermined difference 308. The microprocessor may also alter the output of the laser therapy device when the difference in temperature readings exceeds a predetermined difference 310. Multiple temperature readings may be utilized. There may be more than one predetermined differences where the output is altered by different amounts. This method may be utilized in different manners. Laser therapy is often utilized on damaged tissue. Damaged tissue naturally has a higher temperature than healthy tissue. In this manner the laser therapy device may assist in diagnosing the location of damaged tissue. When the microprocessor determines the location of tissue which is higher in temperature, the microprocessor may alert the operator to the location of tissue which may be irradiated. Alternatively, the microprocessor may automatically energize the laser diode to irradiate the damaged tissue. In addition, the microprocessor may alert an alarm when the temperature drops to signal that the operator is now directing the radiation at healthy tissue. Alternatively, the microprocessor may cease the operation of the laser diode when the temperature drops since the laser therapy device is directed at healthy tissue.

In the preferred embodiment the temperature sensor 4 is a non-contact far infrared array of sensors. The array is configured to take a temperature reading across a wide area of the treatment area 10. The temperature sensor 4 thus can detect a plurality of temperature readings simultaneously. The simultaneous temperature readings on the array can form a pattern of temperature readings formed from some areas in the array detecting higher temperatures than other areas in the array. The microprocessor 6 can determine the pattern of temperature readings from the temperature sensor 4. The microprocessor 6 compares the pattern of temperature readings to known patterns of temperature variations. The known patterns of temperature variations are distinctive of known ailments, tissue damage, or healthy tissue. For instance, temperature readings of an area where veins are close to the surface of the skin would naturally show a difference in temperature readings where the veins are present versus the surrounding tissue. The microprocessor may then generate an alarm signal so that the operator knows to examine the area with greater attention. In other embodiments the microprocessor 6 may alter the output of one or more laser diodes based upon the comparison results. The microprocessor 6 may completely shut down some or all of the laser diodes based upon the measured pattern. Alternatively, the microprocessor 6 may incrementally decrease the output of one or more of the laser diodes based upon the comparison results. Alternatively, the microprocessor 6 may generate an alarm signal based upon the comparison results. The difference between the measured pattern and the known pattern may be determined by a percentage of overlap or any other known method of comparison. An operator may alter the instructions of the microprocessor 6 by establishing a predetermined percentage of overlap to be required before the microprocessor 6 generates an alarm or alters the output of the laser diodes.

In the preferred embodiment of the computerized method for the utilization of the thermal imaging temperature sensor 4 is utilized for diagnostic purposes. In this embodiment the thermal imaging sensor 4 simultaneously measures a plurality of independent temperature readings. The temperature sensor 4 transmits the plurality of independent temperature readings to the microprocessor 6. The microprocessor then determines the existence of one or more features within the plurality of independent temperature readings. As used herein, a "feature" is any grouping, pattern, trait, or attribute of one or more temperature readings within the plurality of independent temperature readings. For instance, and without limiting what constitutes a feature, a feature may include an absolute temperature reading of one or more independent temperature readings; an average temperature reading across multiple independent temperature readings; a grouping of similar temperature readings which exceeds a normal temperature value; a grouping of similar temperature readings which exceeds a predetermined area in size; a temperature gradient; a difference in temperature readings in two points which are within close proximity; a shaped grouping of similar temperature readings; or any other variation within the plurality of independent temperature readings. When the microprocessor determines the existence of a feature, the microprocessor may alter the output of the laser diodes or may generate an alarm signal. In addition, a user may provide instructions to the microprocessor as to what characteristics are required for the designation of a feature.

Figure 8:
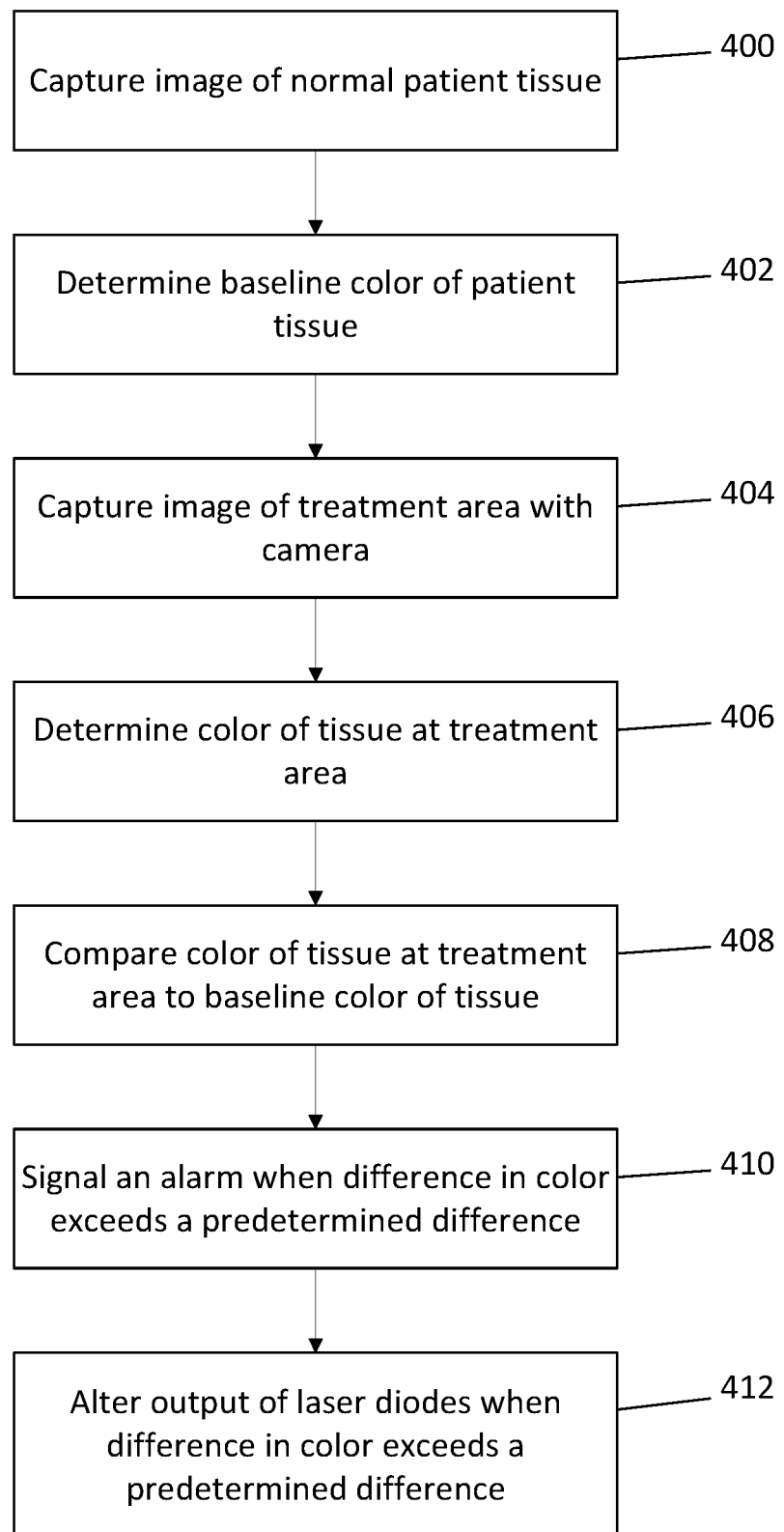
FIG. 8 is schematic of the method of the operation of the laser therapy device.

Referring to FIG. 8, the computerized method of the operation of the color measurement device 5. The color measurement device 5 operates on the principle that damaged tissue is a different color from healthy tissue due to inflammation. The color measurement device captures an image of normal patient tissue 400. The microprocessor then takes a mean average of the color of the patient healthy tissue to generate a baseline reading 402. In another embodiment microprocessor may access a stored database of baseline readings rather than form a new baseline reading. In this manner the color reading of the color measurement device is compared against a stored absolute value rather than against a relative value created by color measurements taken from healthy tissue. The color measurement device captures an image of treatment area 404. The microprocessor then determines the color of the tissue at the treatment area 406. The microprocessor compares the color of the tissue at the treatment area to the baseline color of healthy tissue 408. The microprocessor may cause the laser therapy device to generate an alarm when the difference in color exceeds a predetermined difference 410. The microprocessor may also alter the output of the laser diodes when the difference in color exceeds a predetermined difference 412. This method may be utilized to generate an alarm and/or automatically emit radiation when the operator directs the radiation at damaged tissue. In addition, the method may be utilized to generate an alarm and/or automatically cease the emission of radiation when the operator directs the radiation at healthy tissue. There may be more than one benchmarks used to determine the difference in color such that the laser diodes are altered in increments based on successive incremental differences in color.

The color measurement device 5 can also be utilized to alter the output of the laser diodes based upon absolute value readings received by the color measurement device. For instance, the pigmentation of a user's skin, or the existence of a tattoo, can affect the efficacy of laser therapy treatment. The efficacy of the applied radiation can be improved by altering the output of the laser diodes for optimal treatment of the treatment area. For example, the darker the area to be treated, the lower the output power of the laser diodes and the longer time of treatment. In this manner the color measurement device 5 measures the absolute color reading of the treatment area. Based upon the color reading, the microprocessor can then alter the operations of the laser diodes and operation of the laser therapy device—such as increasing or decreasing the power output of the laser diodes, adjusting the duration of radiation, or otherwise altering the operations of the laser therapy device to increase the efficiency of the operations of the device.

Figure 9:
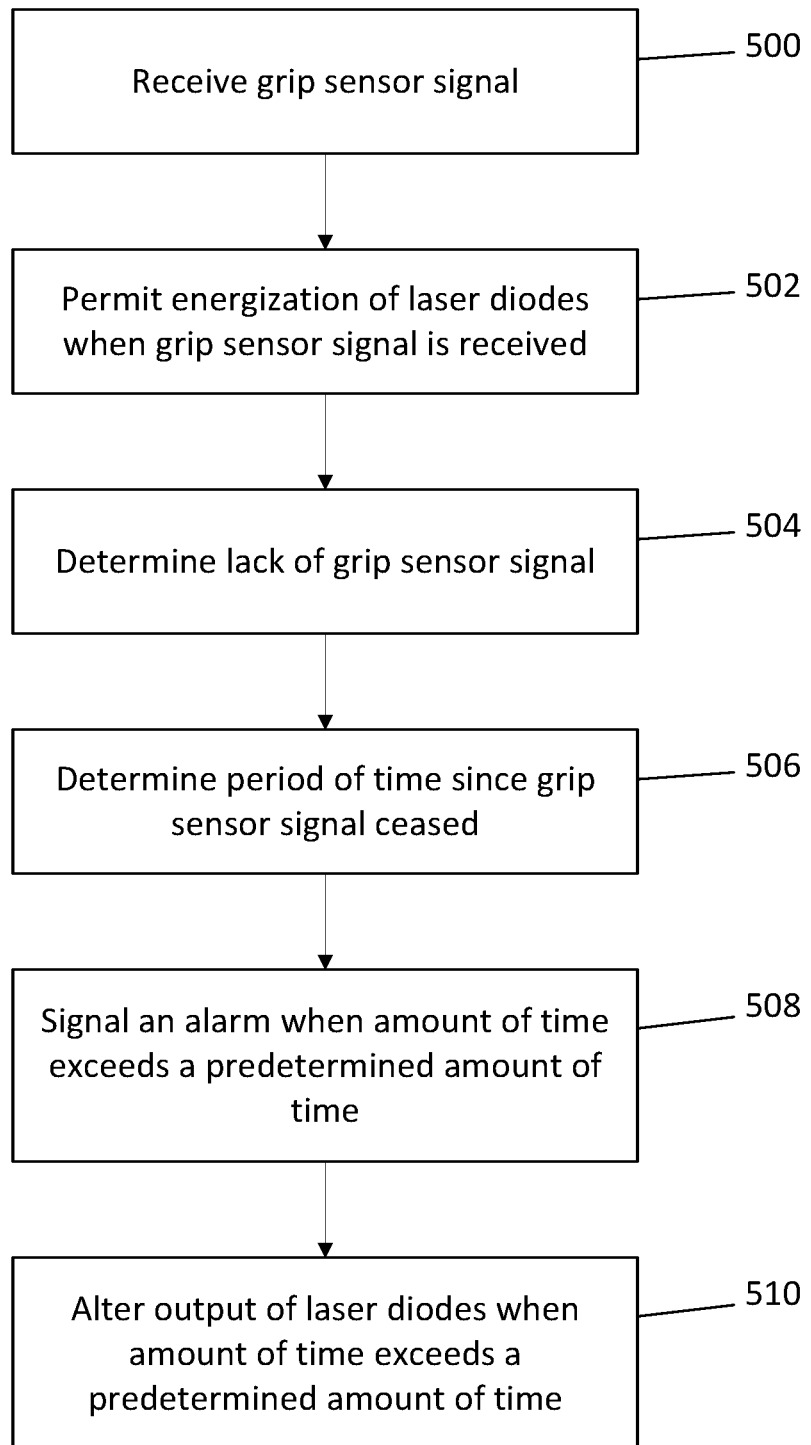
FIG. 9 is schematic of the method of the operation of the laser therapy device.

Referring to FIG. 9, the computerized method for operation of the grip sensor 8. The microprocessor receives a grip sensor signal when the grip sensor is activated 500. The microprocessor permits the energization of the laser diode when the grip sensor signal is received 502. The microprocessor then determines that there is a lack of a grip sensor signal 504. This happens when the user lets go of the grip. The microprocessor may also determine a set period of time from since the grip sensor signal ceased 506. The microprocessor may cause the laser therapy device to generate an alarm when the amount of time exceeds a predetermined amount of time 508. The microprocessor then alters the output of the laser diode when the amount of time since the grip signal ceased exceeds a predetermined amount of time 510.

In any of the computerized methods the microprocessor can adjust the operation of the laser therapy device and output of the laser diodes. The microprocessor 6 can alter or otherwise modify the treatment parameters of the treatment area 10. For instance, the microprocessor 6 can alter the power of the output of the laser diodes, the time for treatment of the treatment area, the optimal distance for treatment, or any other parameter which affects the efficacy of the application of the radiation 13 to the treatment area 10.

What has been described above includes examples of the claimed subject matter. It is, of course, not possible to describe every conceivable combination of components or methodologies for purposes of describing the claimed subject matter, but one of ordinary skill in the art can recognize that many further combinations and permutations of such matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor unit, but, in the alternative, the processor may be any conventional processor, controller, microcontroller, or state machine. A processor may also be implemented as a combination of computing devices, e.g., a combination of a DSP and a microprocessor unit, a plurality of microprocessor units, one or more microprocessor units in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module, which may reside on a tangible, non-transitory computer-readable storage medium. Tangible, non-transitory computer-readable storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a tangible, non-transitory machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A computerized method to be performed by a laser therapy device
    a) wherein said laser therapy device comprises
        i) one or more laser diodes;
        ii) one or more microprocessor units;
        iii) one or more rangefinder units;
    b) wherein said computerized method comprises
        i) emitting one or more laser beam pulses from said one or more rangefinder units;
        ii) receiving, by said one or more rangefinder units, one or more returning target reflections of said one more laser beam pulses;
        iii) determining a time of flight for each of said one or more returning target reflections;
        iv) determining, by said one or more microprocessors, a distance from said one or more laser rangefinder units to a reflecting treatment area, said treatment area being non-circular;
        v) transmitting a distance reading from said one or more laser rangefinder units to said one or more microprocessor units; and
        vi) comparing, by said one or more microprocessor units, said distance reading to a predetermined distance.

2. The computerized method as in claim 1 further comprising altering, by said one or more microprocessor units, a laser output of said one or more laser diodes when said distance reading exceeds one or more predefined distance parameters.

3. The computerized method as in claim 1 further comprising generating, by said one or more microprocessor units, an alarm signal when said distance reading exceeds one or more predefined, distance parameters.

4. The computerized method as in claim 1 further comprising receiving, by said one or more microprocessor units, an instruction to adjust one or more predetermined distance parameters.

5. The computerized method as in claim 2 further comprising generating, by said one or more microprocessor units, an alarm signal when said distance reading exceeds one or more predefined distance parameters.

6. The computerized method as in claim 5 further comprising receiving, by said one or more microprocessor units, an instruction to adjust one or more predetermined distance parameters.

* * * * *